United States Patent
Arora et al.

(10) Patent No.: US 8,926,547 B2
(45) Date of Patent: Jan. 6, 2015

(54) APPLICATOR HAVING A COLOR GRADIENT

(71) Applicant: The Procter & Gamble Company, Cincinnati, OH (US)

(72) Inventors: Kelyn Anne Arora, Cincinnati, OH (US); Ryo Minoguchi, Cincinnati, OH (US); Margaret Henderson Hasse, Wyoming, OH (US); William Hollis Hood, Cincinnati, OH (US); Jeffrey Tupper Roesgen, Anderson Township, OH (US); Colleen Marie Neal, Cincinnati, OH (US); David Andrew Dalton, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 133 days.

(21) Appl. No.: 13/857,176

(22) Filed: Apr. 5, 2013

(65) Prior Publication Data

US 2013/0217960 A1  Aug. 22, 2013

Related U.S. Application Data

(63) Continuation of application No. 12/696,105, filed on Jan. 29, 2010, now Pat. No. 8,435,205.

(51) Int. Cl.
*A61F 13/32* (2006.01)
*A61F 6/12* (2006.01)
*A61F 13/26* (2006.01)

(52) U.S. Cl.
CPC .. *A61F 6/12* (2013.01); *A61F 13/26* (2013.01)

USPC .......................................................... 604/15

(58) Field of Classification Search
CPC .................................................... A61F 13/26
See application file for complete search history.

(56) References Cited

U.S. PATENT DOCUMENTS

| | | | | |
|---|---|---|---|---|
| 4,717,710 A | * | 1/1988 | Shimizu et al. | 503/213 |
| 4,919,983 A | * | 4/1990 | Fremin | 428/35.7 |
| 5,431,697 A | * | 7/1995 | Kamata et al. | 8/483 |
| 5,769,813 A | | 6/1998 | Peiler et al. | |
| 6,676,625 B2 | | 1/2004 | Bernard | |
| 6,924,077 B2 | | 8/2005 | Delp et al. | |
| 7,014,637 B1 | | 3/2006 | Denti et al. | |
| 7,163,528 B2 | | 1/2007 | Christon et al. | |

(Continued)

FOREIGN PATENT DOCUMENTS

| | | |
|---|---|---|
| EP | 684144 A1 | 11/1995 |
| EP | 1279517 A2 | 1/2003 |

(Continued)

OTHER PUBLICATIONS

PCT International Search Report dated Apr. 18, 2011, 4 pages.

*Primary Examiner* — Susan Su
(74) *Attorney, Agent, or Firm* — Andrew J. Hagerty (57) ABSTRACT

An applicator having a color gradient. The applicator includes an outer member having a first end, a second end disposed opposite the first end, a longitudinal axis, a length measured along the longitudinal axis, and an exterior surface. The outer member further includes a color gradient extending along at least a portion of the length from a first region to a second region, the color gradient being visible by a user viewing the exterior surface of the outer member.

7 Claims, 5 Drawing Sheets

(56) References Cited

U.S. PATENT DOCUMENTS

| | | | |
|---|---|---|---|
| 7,166,101 B2 | 1/2007 | Denti et al. | |
| 7,175,616 B2 * | 2/2007 | Denti et al. | 604/11 |
| 7,226,436 B2 | 6/2007 | Gorham et al. | |
| 7,241,274 B2 | 7/2007 | Suga | |
| 7,632,257 B2 | 12/2009 | Magee et al. | |
| 7,875,136 B2 * | 1/2011 | Torstensson et al. | 156/64 |
| 8,075,512 B2 * | 12/2011 | Sargent et al. | 604/15 |
| 2001/0046451 A1 * | 11/2001 | Patel | 422/58 |
| 2002/0183681 A1 * | 12/2002 | Bernard | 604/15 |
| 2003/0073966 A1 | 4/2003 | Sosalla et al. | |
| 2003/0176845 A1 | 9/2003 | Kollwitz et al. | |
| 2003/0181844 A1 * | 9/2003 | Bernard | 604/15 |
| 2005/0096617 A1 | 5/2005 | Gorham et al. | |
| 2005/0148979 A1 | 7/2005 | Palma et al. | |
| 2005/0197617 A1 | 9/2005 | Gorham et al. | |
| 2006/0004319 A1 | 1/2006 | Berg, Jr. et al. | |
| 2006/0004320 A1 | 1/2006 | Berg, Jr. et al. | |
| 2006/0145091 A1 * | 7/2006 | Patel | 250/474.1 |
| 2006/0167430 A1 | 7/2006 | Denti et al. | |
| 2008/0033337 A1 * | 2/2008 | Dougherty et al. | 604/15 |
| 2008/0255496 A1 | 10/2008 | Sargent et al. | |
| 2008/0286483 A1 * | 11/2008 | Khan et al. | 427/510 |
| 2011/0009803 A1 * | 1/2011 | Dougherty et al. | 604/15 |
| 2012/016288 A1 * | 1/2012 | Sargent et al. | 604/11 |

FOREIGN PATENT DOCUMENTS

| | | |
|---|---|---|
| WO | WO 2005082636 | 9/2005 |
| WO | WO 2007141522 | 12/2007 |
| WO | WO 2009081385 A2 * | 7/2009 |

* cited by examiner

APPLICATOR HAVING A COLOR GRADIENT

FIELD OF THE INVENTION

The present invention relates generally to applicators having a gradient, more specifically to applicators for feminine hygiene products having a color gradient.

BACKGROUND OF THE INVENTION

Feminine care products, such as tampons and pessaries, are generally used by women within the vagina, such as, e.g., to absorb menstrual or other body exudates, for pelvic support, and/or for other feminine needs. Such feminine products can be inserted into the vagina digitally, such as, e.g., by using a finger, or can be inserted into the vagina by using an applicator.

Applicators typically comprise an insertion member and a plunger. The material to be expelled from the applicator, such as an absorbent tampon or pessary, can be positioned within the insertion member. The insertion member can have a first end for insertion of the material and a second end for receipt of the plunger. To use the applicator, the consumer will grasp the insertion member, position the first end appropriately, such as, e.g., into the body, and move the plunger in the insertion member towards the first end to insert the material. Some applicators can also include a fingergrip portion that is located on or adjacent to the insertion member, which can allow the consumer to more securely hold the applicator during insertion of a material into the body cavity.

Various applicator configurations have been utilized to facilitate the handling of the applicator and to improve the insertion experience. Currently available configurations, however, are not yet optimized to consistently deliver such benefits. For example, currently available feminine care applicators are generally uniform in color and material with a fingergrip portion that may have a raised and/or depressed configuration of grip elements. In addition, the applicator can include an insertion end that can be tapered and/or include petals. As such, the fingergrip portion and/or the insertion end may not be easily distinguishable from the remainder of the insertion member and the consumer may not be able to appreciate the unique grip and/or insertion end features provided by the applicator.

As such, it would be desirable to provide an applicator having an improved configuration.

SUMMARY OF THE INVENTION

An applicator having a color gradient is provided. The applicator comprises an outer member having a first end, a second end disposed opposite the first end, a longitudinal axis, a length measured along the longitudinal axis, and an exterior surface. The outer member includes a color gradient extending along at least a portion of the length from a first region to a second region, the color gradient being visible by a user viewing the exterior surface of the outer member.

An applicator having a color gradient is also provided. The applicator comprises an outer member having an insertion end, a grip portion positioned opposite the insertion end, a longitudinal axis, a length measured along the longitudinal axis, and an exterior surface. The outer member includes a color gradient extending along at least a portion of the length, the color gradient being visible by a user viewing the exterior surface of the outer member, wherein the color gradient extends along the length of the outer member from a first region substantially aligned with the grip portion to a second region provided towards the insertion end.

An applicator having a color gradient is further provided. The applicator comprises an outer member having a first end, a second end disposed opposite the first end, a longitudinal axis, a length measured along the longitudinal axis, and an exterior surface. The outer member includes a first color gradient extending along at least a portion of the length from a first region to a second region, and a second color gradient extending along at least a portion of the length from a third region to a fourth region, the first and second color gradients being visible by a user viewing the exterior surface of the outer member.

DETAILED DESCRIPTION OF THE INVENTION

Applicators having a color gradient are provided. The applicator can include a color gradient extending along at least a portion of the length from a first region to a second region. In addition, the color gradient is visible by a user viewing the exterior surface of the outer member. In certain embodiments, the color gradient can extend from a dark intensity to a lighter intensity, or vice versa. In addition, or alternatively, in certain embodiments, the applicator can include more than one color gradient along the length of the applicator, such as, for example, a dark to light gradient followed by a light to dark gradient, followed by an additional dark to light gradient, and so on. In certain embodiments, the color gradient can extend from a first color to a second color. The color gradient can be provided on the barrel, the plunger, or both. In certain embodiments, the applicator comprises a light activated pigment. In addition, in certain embodiments, the light activated pigment can be activated using a laser to form a color gradient on the applicator. Such applicator configurations can assist a user in visually identifying features of the applicator, such as, e.g., grip features, and/or insertion features, and/or can assist a user in perceiving other features of the applicator, such as, e.g., insertion comfort, smoothness of insertion, or applicator strength or stability. In certain embodiments, an applicator having a color gradient can assist in masking soiling of the applicator during insertion of the tampon.

As used herein, the term "feminine care product" includes absorbent articles useful for feminine needs, such as articles that typically can be intended for feminine use internally, such as, e.g., within a user's vagina. Internal feminine care products can include, for example, tampons and pessaries.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments.

As used herein, the term "pessary" refers to any type of substantially non-absorbent structure for the purpose of reducing urine leakage and/or supporting a prolapsed uterus and/or bladder. Such pessaries can have any variety of shapes and sizes including cylinder, ovate, spherical, tubular, annual rings, "U" shaped, cup shaped, rings, cubes or donut shaped, and can function in any suitable manner, such as, e.g., by direct application of support, lever force, expansion of the device by selection of material, and/or by inflation of the device.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, "applicator" refers to a device or implement that facilitates the insertion of a feminine care product, such as, e.g., a tampon or pessary, into an external orifice of a mammal. Suitable applicators include, e.g., telescoping, tube and plunger, and compact applicators.

As used herein, the term "insertion end" refers to the portion of the tampon or applicator including the end that is intended to enter the vaginal canal first when inserting the tampon or applicator into the vaginal canal.

As used herein, the term "withdrawal end" refers to the portion of the applicator opposite the insertion end.

As used herein, the term "color" includes any color, such as, e.g., white, black, red, orange, yellow, green, blue, violet, brown, and/or any other color, or declinations thereof.

As used herein, the term "color gradient" refers to a colored region having a first region and a second region, wherein the colored region includes any continuous function in L*a*b* color space. The gradient can be a continuous function of any or all of the L*, a* and/or b* values versus measurement location across or along the samples. In certain embodiments, the gradient can be calculated as $dE^*/dx$, where x is a measure of distance. Using this calculation, areas of solid color measure as a $dE^*/dx$ of less than 1, while a gradient area has $dE^*/dx$ between about 1.5 and about 10, such as, for example, between about 2 and about 5, and discrete colored areas or stripes have $dE^*/dx$ greater than about 5. As such, in certain embodiments, the color gradient as used herein has a $dE^*/dx$ of from about 1.5 to about 5, wherein x is about 0.5.

As used herein, the term "colorfast" refers to the resistance of a material to change in any of its color characteristics, to transfer any of it colorant(s) to adjacent materials, or both, as a result of the exposure of the material to any environment that might be encountered during the processing, testing, storage, or use of the material.

Figure 1:
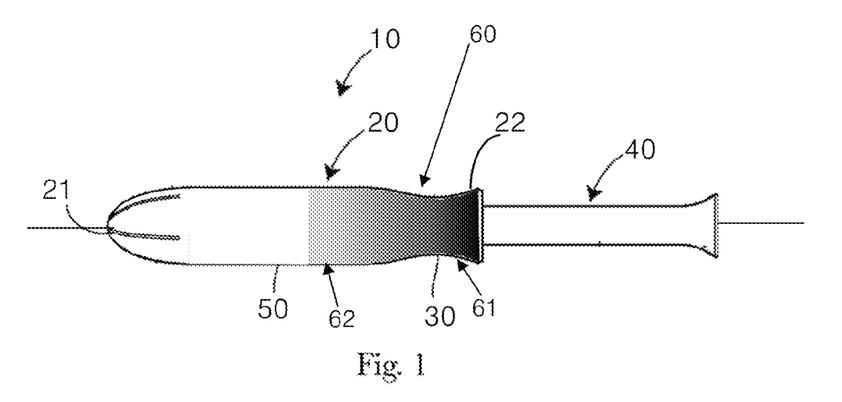
FIG. 1 is a side view of an applicator of the present invention.

FIG. 1 shows one embodiment of an applicator 10. The applicator 10 includes an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 1, the grip portion 30 can be disposed opposite the insertion end 21 of the outer member 20. In addition, the applicator can include a color gradient 60 that can extend from a first region 61 to a second region 62. In certain embodiments, as shown in FIG. 1, the first region 61 can be darker than the second region 62.

Figure 2:
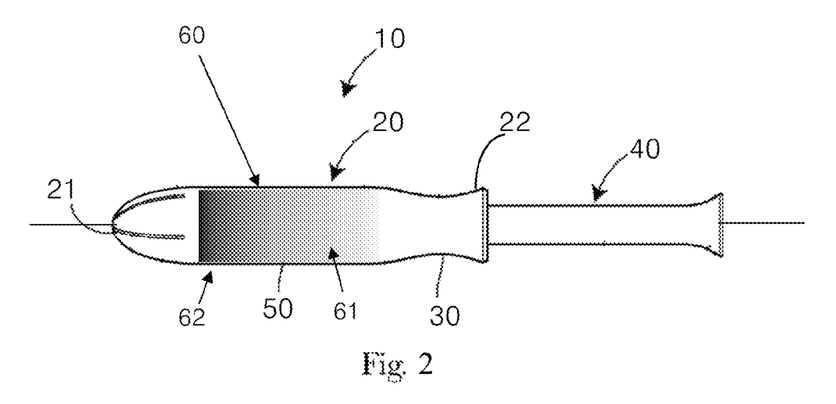
FIG. 2 is a side view of an applicator of the present invention.

FIG. 2 shows one embodiment of an applicator 10. The applicator 10 includes an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 2, the grip portion 30 can be disposed opposite the insertion end 21 of the outer member 20. In addition, the applicator can include a color gradient 60 that can extend from a first region 61 to a second region 62. In certain embodiments, as shown in FIG. 2, the first region 61 can be lighter than the second region 62.

Figure 3:
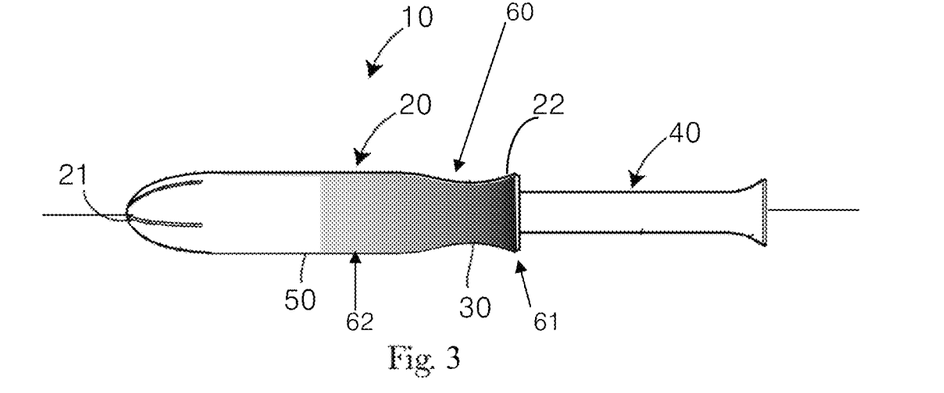
FIG. 3 is a side view of an applicator of the present invention.

FIG. 3 shows one embodiment of an applicator 10. The applicator 10 includes an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 3, the grip portion 30 can be disposed opposite the insertion end 21 of the outer member 20. In addition, the applicator can include a color gradient 60 that can extend from a first region 61 to a second region 62. In certain embodiments, as shown in FIG. 3, the first region 61 can be a first color and the second region 62 can be a second color.

Figure 4:
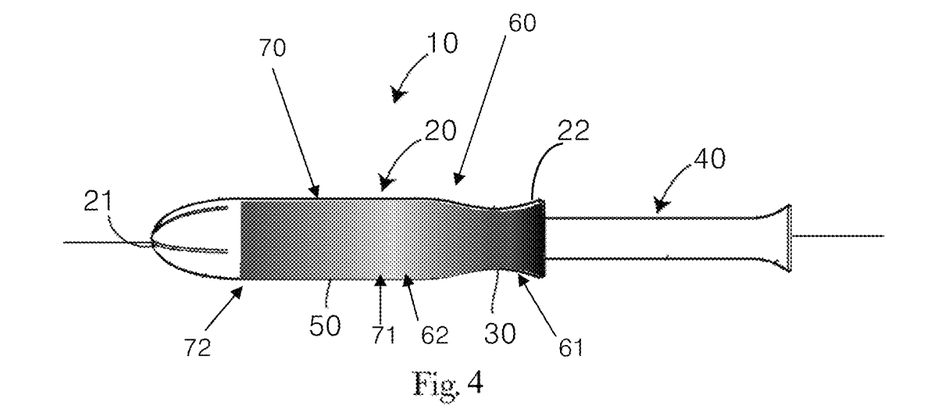
FIG. 4 is a side view of an applicator of the present invention.

FIG. 4 shows one embodiment of an applicator 10. The applicator 10 includes an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 4, the grip portion 30 can be disposed opposite the insertion end 21 of the outer member 20. In addition, the applicator can include a first color gradient 60 that can extend from a first region 61 to a second region 62 and a second color gradient 70 that can extend from a third region 71 to a fourth region 72. In certain embodiments, as shown in FIG. 4, the first region 61 can be darker than the second region 62 and the third region 71 can be lighter than the fourth region 72. In addition, in certain embodiments, the second region 62 and the third region 71 can be substantially the same color and/or intensity. In addition, or alternatively, the first region 61 and the fourth region 72 can be substantially the same color and/or intensity.

Figure 5:
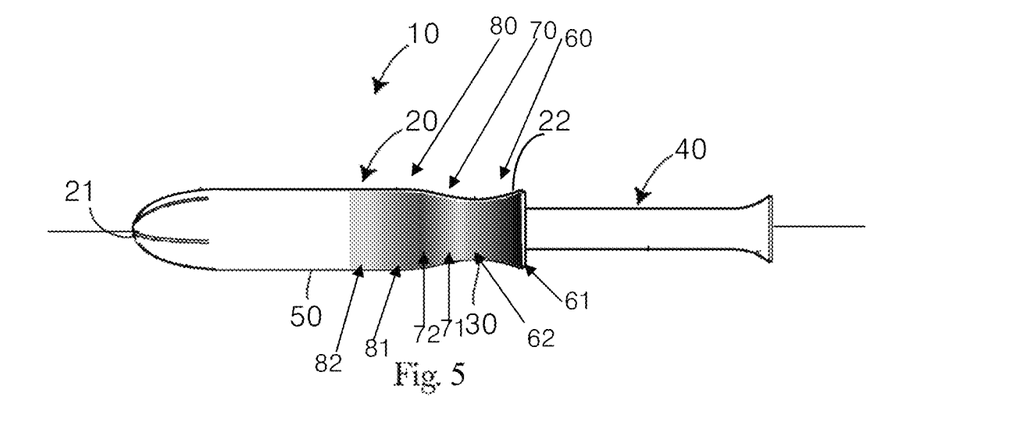
FIG. 5 is a side view of an applicator of the present invention.

FIG. 5 shows one embodiment of an applicator 10. The applicator 10 includes an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 5, the grip portion 30 can be disposed opposite the insertion end 21 of the outer member 20. In addition, the applicator can include a first color gradient 60 that can extend from a first region 61 to a second region 62, a second color gradient 70 that can extend from a third region 71 to a fourth region 72, and a third color gradient 80 that can extend from a fifth region 81 to a sixth region 82. In certain embodiments, as shown in FIG. 5, the first region 61 can be darker than the second region 62, the third region 71 can be lighter than the fourth region 72, and the fifth region 81 can be darker than the sixth region 82.

Figure 6:
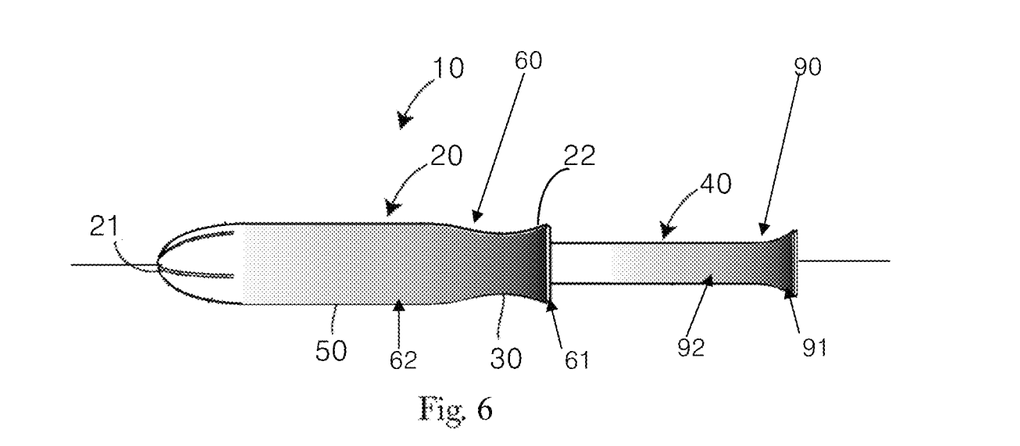
FIG. 6 is a side view of an applicator of the present invention.

FIG. 6 shows one embodiment of an applicator 10. The applicator 10 includes an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 6, the grip portion 30 can be disposed opposite the insertion end 21 of the outer member 20. In addition, the applicator can include a first color gradient 60 on the outer member that can extend from a first region 61 to a second region 62 on the barrel and a second color gradient 90 on the plunger that can extend from a third region 91 to a fourth region 92 on the plunger. In certain embodiments, as shown in FIG. 6, the first region 61 can be darker than the second region 62 and the third region 91 can be darker than the fourth region 92, such that the barrel and plunger each have gradients that are coordinated.

Figure 7:
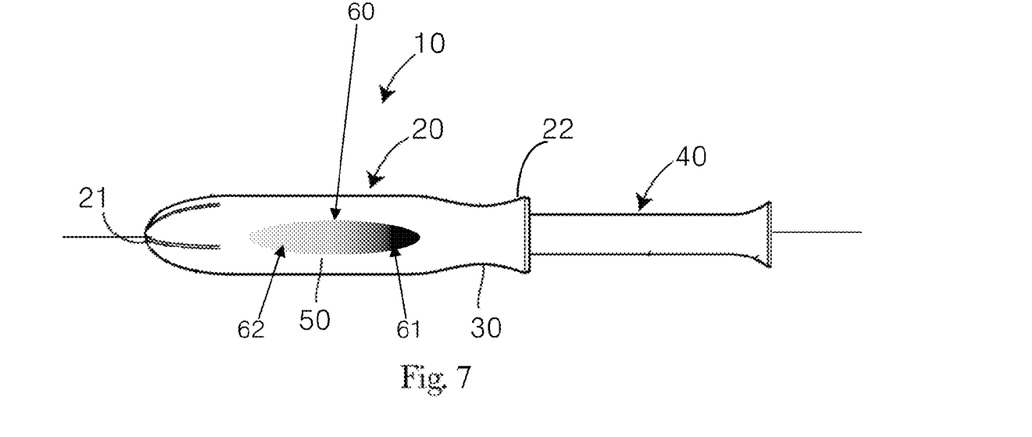
FIG. 7 is a side view of an applicator of the present invention.
Figure 8:
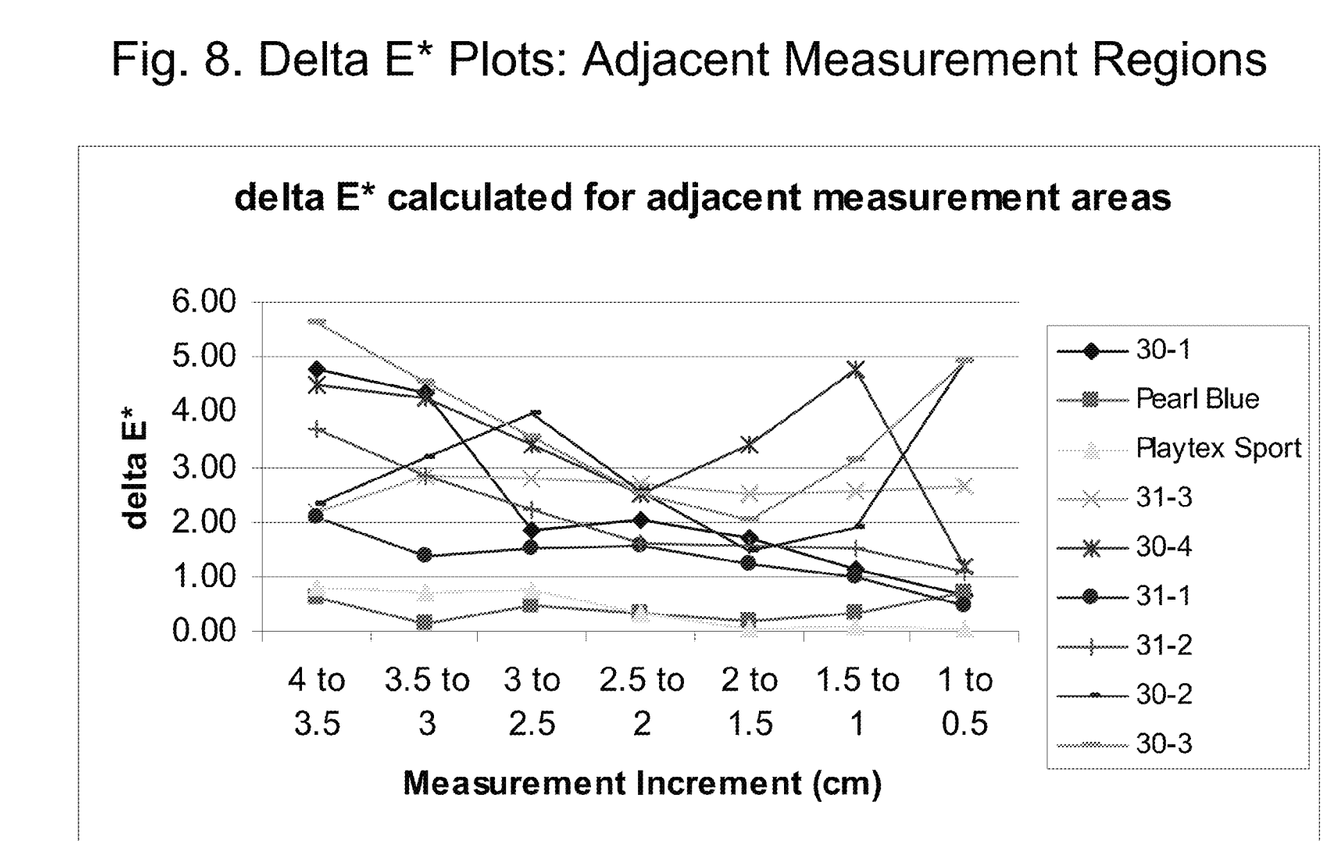
FIG. 8 is a graph of delta E* plots for adjacent measurement regions.

FIG. 7 shows one embodiment of an applicator 10. The applicator 10 comprises an outer member 20, a grip portion 30, a plunger 40, a longitudinal axis (L), and an exterior surface 50. The outer member 20 has a first end 21 that can be the insertion end and a second end 22 that can be the withdrawal end. Alternatively, in certain embodiments, the first end can be the withdrawal end and the second end can be the insertion end. As shown in FIG. 7, the grip portion 30 can be disposed opposite the insertion end 21 of the outer member 20. In addition, the applicator can include a first color gradient 60 that can extend from a first region 61 to a second region 62. In certain embodiments, as shown in FIG. 7, the gradient can be provided in a zone or shape, such as, for example, in the shape of an oval. In addition, as shown in FIG. 7, within the zone or shape, the first region 61 can be darker than the second region 62.

The color gradient can be provided in any suitable configuration, such as, for example, from dark to light and/or light to dark within a color, from color to color with similar intensity, from dark to light and/or light to dark from color to color, or in any other suitable configuration. In certain embodiments, the gradient can be provided from the grip region of the applicator, along the barrel, and to the insertion end of the applicator. In addition, or alternatively, a gradient can be provided on the plunger, such as, for example, from the withdrawal end of the plunger to the insertion end of the plunger. In certain embodiments, a gradient can be provided on both the barrel and on the plunger.

The gradient is "visually perceptible" to a viewer. By "visually perceptible" is meant that a human viewer can visually discern the gradient with the unaided eye (excepting standard corrective lenses adapted to compensate for nearsightedness, farsightedness, or stigmatism, or other corrected vision) in lighting at least equal to the illumination of a standard 100 watt incandescent white light bulb at a distance of 0.25 meter. In certain embodiments, the gradient is greater than about 0.3 cm, such as, for example, greater than about 0.5 cm, greater than about 1 cm, greater than about 2 cm, or any other suitable length.

The gradient can include any suitable color, such as, for example, white, black, red, orange, yellow, green, blue, violet, brown, and/or any other color, or declinations thereof. In certain embodiments, the gradient can be a gradient from blue to white, blue to clear, darker blue to lighter blue, pink to white, pink to clear, darker pink to lighter pink, purple to white, purple to clear, darker purple to lighter purple, blue to purple, pink to purple, or any other suitable configurations.

A color gradient may be identified by $\Delta E$ values along the length or the gradient, which are mathematically expressed by the equation:

$$\Delta E^* = [(L^*_X - L^*_Y)^2 + (a^*_X - a^*_Y)^2 + (b^*_X - b^*_Y)^2]^{1/2}$$

'X' represents a first measuring point and "Y" represents a second measuring point along the gradient.

The color scale values utilized herein to define the gradient are the CIE LAB scale. Measurements are made with a Hunter Color reflectance meter. A complete technical description of the system can be found in an article by R. S. Hunter, 'photoelectric color difference Meter', Journal of the Optical Society of America, Vol. 48, pp. 985-95, 1958. Devices specially designed for the measurement of color on the Hunter scales are described in U.S. Pat. No. 3,003,388 to Hunter et al., issued Oct. 10, 1961. In general, Hunter Color "L" scale values are units of light reflectance measurement, and the higher the value is, the lighter the color is since a lighter colored material reflects more light. In particular, in the Hunter Color system the "L" scale contains 100 equal units of division. Absolute black is at the bottom of the scale (L=0) and absolute white is at the top of the scale (L=100). Thus, in measuring Hunter Color values of the applicators according to the present invention, the lower the "L" scale value, the darker the material. The applicators herein might be of any color provided that the L Hunter value defined herein is met. When a color is defined according to this system L* represents lightness (0=black, 100=white), a* and b* independently each represent a two color axis, a* representing the axis red/green (+a=red, −a=green), while b* represents the axis yellow/blue (+b=yellow, −b=blue).

The color gradient can be provided at any suitable location on the applicator. For example, in certain embodiments, the color gradient can extend from the grip portion to the insertion end. Alternatively, the color gradient can extend along only a portion of the length of the applicator. In certain embodiments, a series of color gradients can be provided along the length of the applicator. Such gradients can be contiguous or separate. In addition, the color gradient can extend around any suitable amount of the circumference of the applicator, such as, e.g., a portion of the circumference of the applicator or substantially the entire circumference of the applicator.

The color gradient can be provided in any suitable manner. In certain embodiments, the color gradient can be provided by applying color after formation of the applicator, such as, e.g., by the application of ink, shrink wrap, film, deposition, etching or bleaching. In addition, or alternatively, the color gradient can be provided by applying color during formation of the applicator, such as, e.g., by use of resin incorporated pigments or activatable colorants or by comolding. Activatable colorants are materials which provide a color change in response to an external stimulus such as electromagnetic radiation, light, heat or pressure. A gradient in color could therefore be created through selective gradation of the external stimulus. For example, an applicator could be molded comprising a light activated colorant that will change color upon exposure to light. By changing the intensity or duration of light exposure along the length of the applicator, a color gradient can be created. Alternatively, an applicator could be printed with varying intensity of color.

In certain embodiments, the applicator comprises an activatable colorant. The activatable colorant can produce a color change that is reversible or irreversible. In certain embodiments, the activatable colorant produces a color change that is irreversible, thereby providing a permanent visual effect. Sources of activatable colorants include 'thermochromic', which means that the color change is induced by a change of temperature, or 'photoreactive', which means that the color change is induced by electromagnetic radiation, or 'piezochromic', which means that the color change is induced by pressure. Each of these sources of activatable colorants is discussed more fully below.

Combinations of the aforementioned mechanisms in the color change material are also within the scope of the present invention. The color change materials herein can either be coated onto parts of the applicator, or can form an integral part of components of the absorbent article by being added e.g. to the polymeric master batch these components are made of. The color change materials herein change their color in response to external stimuli as defined hereinbefore.

a) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is 'ChromaZone® Thermobatch Concentrates available from Thermographic Measurements Co. Ltd. Thermochromic pigments and the mechanism bringing about the temperature triggered color change are well-known in the art and are for example described in U.S. Pat. No. 4,826,550 and U.S. Pat. No. 5,197,958. Other examples of thermochromic pigments are described in published US application 2008/0234644A1.

Alternatively, the thermosensitive pigment may be of a microcapsule type which is known in the art of thermosensitive pigments.

b) Piezochromic Materials

Any piezochromic materials disclosed in the art are suitable herein as long as they meet the necessary health and safety requirements. An example is disclosed in U.S. Pat. No. 6,330,730.

In one example the piezochromic material is thermochromic and responds to a temperature increase caused by applied pressure. In another example the piezochromic material comprises a dye, which is encapsulated into microcapsules. Upon application of pressure these capsules break and release the dye, which then becomes visible. The color intensity is directly linked to the amount of pressure applied. Typical piezochromic materials require a pressure of from 14 to 140 kPa.

Most typically piezochromic color change materials change their color in an irreversible fashion after exertion of pressure. This is due to the fact that the color change was achieved by the destruction of microcapsules, in which the substances for achieving the color change were encapsulated.

c) Photoreactive Materials

Photoreactive materials change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transiting from a colorless state to a color state upon exposure to light and back to a colorless state when reversed. Examples for photochromic materials are described in U.S. Pat. No. 6,306,409; U.S. Pat. No. 6,080,415 or U.S. Pat. No. 5,730,961.

Polychromic materials are those which are capable of generating multiple colors. Compounds based upon diacetylene, X—C≡C—C≡C—Y, when polymerized, are known to take on different color properties. Polymerization is typically achieved by exposure to certain types of radiation, such as ultraviolet radiation. Varying the intensity of the radiation causes differing degrees of polymerization, and different colors.

It is known that these properties can be utilized to achieve multi-color printing. See, for example; U.S. Pat. No. 4,705,742, "Processless Multicolour Imaging", issued on Nov. 10, 1987, assigned to Gaf Corporation; and WO2006/018640, "Multi-colour printing", published on Feb. 23, 2006, Sherwood Technologies Ltd. Both of these documents disclose methods of applying coatings comprising various diacetylene compounds to the surface of a substrate for the purpose of irradiating and forming an image on the surface of the substrate.

Particularly preferred materials are those that can be dispersed or blended into the polymeric matrix of the layers, such as those disclosed in PCT publication WO 2009/093028A2 and WO 2009/081385 A2, which are compounds which undergo a color change upon irradiation, and which have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1.

Another example of a material of use in the present invention is a thermoplastic material comprising polymer mixed with a charge transfer agent and a photo acid generating agent such as those described in US 2009/0191476 A1. Exposure of the thermoplastic material comprising the charge transfer agent and photo acid generating agent to irradiation will bring about a color change reaction which can be used to create text, artwork, devices or other images and effects.

In certain embodiments, the applicator comprises photoreactive materials providing an irreversible, permanent change in color. Examples of photoreactive materials providing permanent color change are described in PCT publication WO 2009093028A2 which describes polychromic substances comprising diacetylene compounds that change color when subjected to irradiation. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Ultraviolet irradiation is preferred for changing substrates comprising the diacetylene compounds from colorless or low visual color to color on exposure to ultraviolet irradiation, and then change to a color different to the first on subsequent exposure to infrared irradiation. Laser irradiation may be preferred for writing text and drawing intricate artwork directly on substrates comprising the diacetylene compounds, as laser imaging can be conveniently controlled by computer with the appropriate software and has superior resolution capability. However, similar effects can be obtained by passing radiation from, for example, an ultraviolet lamp through a mask before it reaches the substrates comprising the diacetylene compound.

Another application describing of photoreactive materials providing permanent color change includes WO 2009/081385 which describes thermoplastic material comprising polychromic substance wherein the polychromic substance is a functionalized diacetylene having a formula which has a general structure that is described therein.

Activation of photoreactive materials is preferably achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A.

Other examples of equipment that may be used for activation of photoreactive materials include the J3825 MonoCure Lamphead from Nordson UV Limited (Berkshire UK) and the 270S UV Lamp Assembly and Power Supply by Integrated Technology. The type of lamp within the unit may be changed to vary the spectral output as needed. Examples of relevant bulb types include "H", "V", "D" and "Q".

The applicator, including the outer member, the grip portion, and the inner member can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanoate, ethylene vinyl acetate, polyurethane, silicone, thermoplastic starch, trans-poly isoprene, derivatives thereof, copolymers thereof, mixtures thereof, or any suitable smooth plastic material. Examples of suitable materials are disclosed in, e.g., U.S. Pat. Nos. 5,346,468 and 5,558,631. In certain embodiments, additives can be included in the material to alter or enhance certain material properties. Suitable additives include, for example, mold release agents, slip agents, surface energy modifiers, UV absorbers, inorganic fillers and/or any other suitable additives. In certain embodiments, the outer member can be coated with a substance to give it a high slip characteristic, such as, e.g., with wax, polyethylene, a combination of wax and polyethylene, cellophane, clay, and other lubricants that can facilitate comfortable insertion.

The outer member can be sized and configured to house a feminine hygiene product, such as, e.g., an absorbent tampon and/or pessary. In certain embodiments, the size of the outer member can be determined primarily by the dimensions of the feminine hygiene product. For example, the outer member can have inner diameters of about 5.0 millimeters to about 22.0 millimeters and a wall thickness of about 0.2 millimeter to about 2.0 millimeters. The inner diameter of the outer member can be greater than the diameter of the feminine hygiene product to prevent the outer member from interfering with the expulsion of the feminine hygiene product from the barrel portion. In certain embodiments, the inner diameter of the outer member can have varying diameters and shapes to conform to the profiled shape of the enclosed feminine hygiene product, such as, e.g., a tampon. The outer member can have a length sufficient to house the feminine hygiene product prior to the expulsion of the feminine hygiene product from the applicator into the vagina.

The outer member can be of any suitable cross-sectional shape. In certain embodiments, the outer member can include a generally non-circular cross-sectional shape, such as, e.g., oval, rectangular, elliptical, oblate, or other suitable shapes. The outer member can have a cross-sectional shape that has a greater thickness than width or vice versa. In certain embodiments, the outer member can have a substantially uniform cross-section, such as, e.g., having the same cross-section along the length. In other embodiments, the outer member can have varying cross-sectional shapes and/or cross-sectional sizes, such as, e.g., a outer member having a smaller cross-sectional area near the insertion end of the barrel and a larger cross-sectional area near the opposite end.

The insertion end of the outer member can be open-end or closed-ended. In certain embodiments, the insertion end of the outer member can include petals, corrugations, pleats, a film cap, or other means for covering the outer member prior to explusion of the tampon. In certain embodiments, the material, such as, e.g., a feminine care product can be loaded into the outer member prior to covering the insertion end of the barrel portion. Alternatively, the insertion end of the outer member can be covered prior to loading the feminine hygiene product into the barrel portion.

The grip portion can provide for secure handling of the applicator. The perimeter of the grip portion can be any suitable shape, such as, for example, oval, circular, arc, concave, cone convex, diamond, line, polygon, rib, square, triangle, rectangular, or any combination thereof. The grip portion can include projections, depressions, texturing, embossments, grooves, treads, and/or raised surfaces. Such surfaces can be created by impressing or compressing the surfaces. In certain embodiments, the grip portion can include one or more flattened sides and/or one or more spaces for a decorative marking or a character. In addition, or alternatively, the surfaces of the grip portion can include a material that can provide a frictional resistance for the user's fingers during the insertion of the tampon applicator into the body. Suitable materials that can provide friction include, for example, abrasive materials, high wet coefficient of friction materials, pressure sensitive adhesives, or any combinations thereof. In certain embodiments, the surfaces of the grip portion can include a material that can improve the feel of the grip to a user, such as, e.g., one or more compressible materials, such as, e.g., rubber, silicone, and/or foam. In certain embodiments, the grip portion shape can correspond to the outer member shape. Alternatively, the grip portion can be a different shape than the barrel portion.

In certain embodiments, the grip portion can be a same material as the barrel portion. Alternatively, the grip portion can be one or more different materials as compared to the barrel portion. The grip portion can also comprise one or more compressible materials, such as, e.g., rubber, silicone, and/or foam, and/or one or more soft plastics. In certain embodiments, the grip portion can have a substantially rigid inner surface and a deformable outer surface, such as, e.g., to improve user comfort while substantially preventing compression of the interior of the grip, such as, e.g., to allow the plunger to move in the axial direction while the outer surface of the grip is deformed by a user's fingers.

The plunger can be hollow or solid. In certain embodiments, the plunger can have a hollow interior, a first end, and a second end opposed to the first end. The first end is the portion of the plunger that pushes against the tampon during the expulsion of the tampon from the barrel portion. The second end is the portion of the plunger in which the axial force is applied to expel the tampon from the barrel portion. In certain embodiments, the plunger can have a locking mechanism, such as, e.g., a locking mechanism that retains the plunger within the outer member and/or grip portion of the applicator prior to depression of the plunger and expulsion of the tampon. Examples of such locking mechanisms are described in, for example, U.S. Pat. Nos. 6,019,744 and 6,450,986.

In certain embodiments, the plunger can be an optional component for use with the applicator. For example, the applicator can be fully functional if the plunger is omitted, i.e., if a user must insert and push the feminine hygiene product through the tampon applicator digitally.

In certain embodiments, at least a portion of the applicator can contact and/or conform to at least a portion of the surface of the tampon. Rigid insertion end structures can be shaped in a suitable manner, such as, e.g., by injection molding, or by reshaping in a secondary process to provide at least a degree of profiled shape observation. Alternatively, insertion ends of applicators made from flexible or pliable materials, such as films, paper and flexible wovens or non-wovens, can also be used. Such flexible or pliable insertion ends include those which partially or fully enclose the tampon comprising a "sleeve" or a "tube," such as, e.g., in U.S. Pat. Nos. 2,922,422 and 2,922,423; a "sheath," such as, e.g., in U.S. Pat. Nos. 2,092,427 and 3,749,093; a "barrel," such as, e.g., in U.S. Pat. No. 5,135,475; a "bag," such as, e.g., in U.S. Pat. No. 3,358,686; or a "film enclosure," such as, e.g., in U.S. Pat. No. 4,610,659.

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

This example demonstrates a method for preparing a tampon applicator having a color gradient.

A tampon applicator was injection molded using low-density polyethylene from Marlex® KN226 low-density polyethylene (Chevron Phillips Chemical Company LP, The Woodlands, Tex.) and 0.25 wt % Datalase Colour Change Pigment HT (Datalase, Ltd., Widnes, ENGLAND). The initial applicator color was white.

The applicator was then exposed to UV light to create a gradient of color ranging from nearly white at the petal end to blue at the grip portion, using a UV lamp having a metal enclosure containing 8 UV amalgam lamps and 8 ballasts with individual circuits for individual lamp controls and a fan for cooling lamps to maintain temperature. The lamps are 357 mm in length and are available from American Ultraviolet (Lebanon, Ind.) as part number GML750A.

Activation was achieved by placing the applicator in an assembly including a ramp, an adjustable shield and a shuttle. The angle of the ramp was adjusted to 2° to control the dwell time under the UV light. The shield progressively exposed less of the applicator to the UV light as the applicator rolled along the ramp, resulting in a color gradient. The applicator was activated by placing it on the shuttle, placing the shuttle in the tracks on the ramp and releasing the shuttle so that the applicator rolls under the lamps. When the shuttle comes out the other end of the unit, the applicator was activated and a color gradient had been formed.

Example 2

This example demonstrates preparation of a tampon applicator having a color gradient.

A tampon applicator was injection molded comprising low-density polyethylene and 1 wt % Datalase Colour Change Pigment LT. Using the UV lamp described in Example 1, the applicator was rotated by hand under the lamp with the grip end directly under the bulbs and the petal end not directly under the bulbs. The resulting sample was dark blue at the grip and nearly clear at the petals.

Example 3

This example demonstrates preparation of a tampon applicator having a color gradient.

A tampon applicator was prepared as in Example 2 and was subsequently heated with a heat gun, which changed the color of the applicator so that it is now exhibits a gradient from red at the grip end to pink at the petal end.

Example 4

This example demonstrates preparation of a tampon applicator having a color gradient.

A tampon applicator was injection molded using low-density polyethylene and 1 wt % Datalase Colour Change Pigment LT. The applicator was rolled under the UV lamp described in Example 1, except that no shield was in place, so the applicator turned a uniform blue color. The applicator was then heated with a heat gun directed only at the grip end. The resultant applicator has a grip that is red, transitioning to purple in the middle to blue at the petal end, demonstrating a gradient from one color to a different color.

Example 5

This example demonstrates preparation of a tampon applicator having a color gradient.

A tampon applicator was injection molded using low-density polyethylene and 0.25 wt % Datalase Colour Change Pigment HT. The initial applicator color was white. A blue gradient was created on the applicator by rolling it under the lamp with all 8 bulbs turned on in the UV lamp described in Example 1. The applicator was rolled under the lamp 5 times with the shielding plate covering all but the grip portion.

Example 6

This example demonstrates preparation of a tampon applicator having a color gradient.

A tampon applicator with a blue gradient was created as described in Example 5, except the shielding plate was moved to expose the grip portion plus 1 cm of the barrel. The applicator was rolled under the lamp once with the shielding plate covering all but the grip portion plus 1 cm of the barrel.

Example 7

This example demonstrates preparation of a tampon applicator having a color gradient.

A tampon applicator with a blue gradient was created as described in Example 6, except the applicator was rolled under the lamp 5 times.

Example 8

This example demonstrates preparation of an applicator plunger having a color gradient.

A plunger for a tampon applicator was molded using low-density polyethylene and 0.25 wt % Datalase Colour Change Pigment HT. The plunger was rotated by hand for 10 seconds with half of its length directly under the lamp. The resulting sample had a gradient in color from blue to white.

Example 9

This example demonstrates measurement of the color gradient of the tampon applicators prepared in Examples 1-8.

For measuring the L*, a*, and b* values for the invention herein, a standard, industry-recognized procedure is used. The topsheet color is measured using a reflectance spectrophotometer in accordance with method ASTM E 1164-94, "Standard Practice for Obtaining Spectrophotometric Data for Object-Color Evaluation". This standard method is followed but specific instrument settings and sampling procedure are given here for clarity. Sample color is reported in terms of the CIE 1976 color coordinate standard as specified in ASTM E 1164-94 and ASTM D2264-93, section 6.2. This consists of three values; L* which measures sample "lightness", a* which measures redness or greenness, and b* which measures yellowness or blueness.

L* a* b* values were measured by using a Hunter LabScan XE Reflectance Spectrophotometer available from Hunter Associates Laboratory, Inc., Reston, Va., according to following conditions and procedure.

a) Setting Parameters for Hunter LabScan XE Reflectance Spectrophotometer:

Illuminant=D65

Observer=10

Geometry=0/45

UV Filter=Nominal

Port Size=0.20 in. (0.508 cm)

Area View=0.125 in. (0.3175 cm)

b) Calibration Procedure:

The white standard tile #LX16566 and the green diagnostic tile were prepared with specified X, Y, and Z values in the CIE 1931 XYZ color space. The port aperture of the Hunter Spectrophotometer was completely covered with these tiles and X, Y, and Z values for each tile were measured. The Hunter Spectrophotometer was calibrated such that X, Y, and Z values for the white standard tile were within ±0.30 color units, and X, Y and Z values for the green diagnostic tile were within ±0.15 color units.

c) Measurement Procedure:

The applicator was cut longitudinally and top-weighted with a 10 lb. static weight such that the samples were held flat against the port aperture of the Hunter Spectrophotometer. The white standard tile was used as a flat backing. L*a*b* values in the CIE 1976 L*a*b* color space were recorded every 0.5 cm along the gradient. $\Delta E^* = [(L^*x - L^*y)^2 + (a^*x - a^*y)^2 + (b^*x - b^*y)^2]^{1/2}$ was calculated for adjacent measurements and the calculated $\Delta E^*$ was divided by the distance between the two points to determine the color gradient ($\Delta E^*/d$). In addition, L* a* b* values viewed independently for continuous behavior to differentiate a gradient from discrete printed regions.

The following applicators were measured: commercially available Tampax® Pearl blue applicator, commercially available Playtex® Sport light green applicator, blue applicator with green discrete printed areas, applicator with a blue gradient as prepared in Example 2 (30-2), applicator with a red gradient as prepared in Example 3 (30-3), applicator with a blue gradient as prepared in Example 4 (31-2), applicator with blue gradient as prepared in Example 5 (31-1), applicator with a red to blue gradient as prepared in Example 6 (30-4), applicator with a blue gradient as prepared in Example 7 (31-3), and applicator with a blue to white gradient as prepared in Example 8 (30-1). The results are shown in Table 1:

TABLE 1

$\Delta E^*$ for Adjacent Measurement Areas

| Sample | Measurement distance from petal (cm) | | | | | | |
|---|---|---|---|---|---|---|---|
| | 4 to 3.5 | 3.5 to 3 | 3 to 2.5 | 2.5 to 2 | 2 to 1.5 | 1.5 to 1 | 1 to 0.5 |
| Pearl Blue | 0.61 | 0.12 | 0.49 | 0.31 | 0.18 | 0.31 | 0.71 |
| Playtex Sport | 0.81 | 0.72 | 0.75 | 0.33 | 0.07 | 0.11 | 0.05 |
| Pearl Printed | 3.96 | 5.68 | 26.92 | 33.97 | 19.85 | 19.33 | 0.33 |
| 30-2 | 2.30 | 3.16 | 3.97 | 2.53 | 1.45 | 1.91 | 4.91 |
| 30-3 | 5.63 | 4.55 | 3.57 | 2.52 | 2.03 | 3.10 | 4.89 |
| 31-2 | 3.66 | 2.85 | 2.23 | 1.63 | 1.57 | 1.49 | 1.07 |
| 31-1 | 2.07 | 1.38 | 1.51 | 1.58 | 1.25 | 0.99 | 0.48 |
| 30-4 | 4.47 | 4.23 | 3.41 | 2.52 | 3.42 | 4.79 | 1.19 |
| 31-3 | 2.17 | 2.84 | 2.77 | 2.71 | 2.50 | 2.54 | 2.64 |
| 30-1 | 4.79 | 4.33 | 1.86 | 2.03 | 1.72 | 1.13 | 0.66 |

As shown in Table 1, both Tampax® Pearl Blue and Playtex® Sport have no visible gradient and have $\Delta E^*$ values<1 for every measurement increment. Gradient samples 30-2, 21-2, 31-1, 30-4, and 30-1 have $\Delta E^*$ values>1 for every measurement increment, and gradient samples 30-3 and 31-3 have $\Delta E^*$ values>2 for every measurement increment. In contrast, the Pearl Printed sample demonstrates regions having $\Delta E^*$ values>5, regions having $\Delta E^*$ values>10, and even regions having $\Delta E^*$ values>20. Therefore, this example demonstrates that monitoring L*, a*, b* for each measurement increment allows differentiation between continuous color changes (i.e., gradients) and discrete regions of color (i.e. image printing or color bands).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator for feminine care products, the applicator comprising:
   a. an outer member comprising a first end that defines an insertion end and a second end that defines an withdrawal end;
   b. a grip portion disposed proximate the second end;
   c. wherein the first end comprises an injection moldable polymeric material that includes an activatable colorant incorporated therein;
   d. wherein the grip portion comprises a grip material that is different from the injection moldable polymeric material of the first end; and
   e. wherein some of the activatable colorant is activated.

2. The applicator of claim 1, wherein injection moldable polymeric material is selected from the group comprising a polyethylene, a polypropylene, and mixtures thereof.

3. The applicator of claim 1, wherein the grip material is compressible.

4. The applicator of claim 1, wherein the grip material is selected from the group comprising a rubber, a silicone, a foam, and mixtures thereof.

5. The applicator of claim 1, wherein the grip portion comprises a substantially rigid inner surface and a deformable outer surface.

6. The applicator of claim 1, wherein the activatable colorant comprises a photoreactive material.

7. The applicator of claim 1, wherein the activatable colorant comprises a diacetylene.

* * * * *